United States Patent [19]

Matravers

[11] Patent Number: 4,996,239

[45] Date of Patent: Feb. 26, 1991

[54] WATER RESISTANT CREAM CONDITIONER

[75] Inventor: Peter Matravers, San Marino, Calif.

[73] Assignee: Neutrogena Corporation, Los Angeles, Calif.

[21] Appl. No.: 245,660

[22] Filed: Sep. 16, 1988

[51] Int. Cl.$^5$ ............................ A61K 7/48; A61K 9/07
[52] U.S. Cl. .................................... 514/873; 514/943; 514/969
[58] Field of Search ................ 514/873, 857, 943; 424/59, 60, 865

[56] References Cited

U.S. PATENT DOCUMENTS

| | | | |
|---|---|---|---|
| 4,368,187 | 1/1983 | Flom et al. | 514/847 |
| 4,423,041 | 12/1983 | Clum et al. | 424/68 |
| 4,435,384 | 3/1984 | Warren | 424/101 |
| 4,749,563 | 6/1988 | Georgalas | 514/873 |

OTHER PUBLICATIONS

Cosmetics & Toiletries, 11/1986, vol. 101, pp. 148-150 and 152.

Primary Examiner—Dale R. Ore
Attorney, Agent, or Firm—Richard R. Mybeck

[57] ABSTRACT

A skin protective composition for exhibiting enhanced water repellency and conditioning effects containing aliphatic waxes and hydrophobic silicones in a nonallergenic, non-toxic, cosmetically acceptable carrier. The composition is useful to protect mammals from solar radiation and in the treatment of diaper rash.

4 Claims, No Drawings

WATER RESISTANT CREAM CONDITIONER

The present invention relates generally to a water resistant cream conditioner and more particularly to a novel skin protective composition containing aliphatic waxes and hydrophobic silicones admixed into a nonallergenic, nontoxic cosmetically acceptable carrier. This combination exhibits surprisingly enhanced water repellency and skin conditioning effects while substantially eliminating the greasy appearance and tacky feel normally associated with water barrier products. Unexpectedly, the composition also enhances moisturization at a level that is far superior to conventional diaper creams.

BACKGROUND OF THE INVENTION

In an attempt to improve product substantivity on skin surfaces, the prior art has traditionally used cationic fatty derivatives, quaternary ammonium salts, resins and gums as additives in cream/lotion bases. Little work has been done to improve the emulsion base itself apart from routine product stability adjustments. In recent years, raw material vendors flooded the market with these additives to further complicate the dilemma. Indeed the formulation of good cream/lotions has become secondary to the incorporation of these inelegant additives to create compositions which neither look nor feel like cosmetic creams. Instead, they are very sticky, and leave an uncomfortable feel throughout the usage period. User compliance with such compositions is therefore quite poor. Moreover, the use of certain cationic/quaternary ingredients will cause skin and eye irritations. In addition resins and gums can cause "powdering" upon drying from too great a friability which further contributes to poor product appearance and inferior skin substantivity.

As a result, many products on the market today give the consumer a false sense of security because of the inability of the active ingredients thereof to remain in place when the user is engaged in water activities, or encounters rain or other liquids which literally wash the active ingredients away.

The present invention comprises an effort to address this problem and provide elegant topically applied preparation which is water repellent, moisturizes the skin, and further serves as a novel drug delivery system in which sunscreens, and like topically effecting drugs/chemicals can be applied to human skin. The base composition of the present invention can be formulated to provide a variety of cosmetic, presonal care and/or pharmaceutical preparations, such as hand creams, lip balm, facial cosmetics, diaper creams, ostomy creams, medicinal creams and the like. Thus, a preparation is herein described which possesses many positive attributes including superior water repellency, resistance to being washed off, physiological mildness, and a pleasant feel which enhances user comfort and hence, user compliance.

BRIEF SUMMARY OF THE INVENTION

The present invention relates to a pharmaceutical/cosmetic preparation form in a base containing a synthetic aliphatic wax, that is, a high molecular weight $C_{18}$–$C_{36}$ saturated synthetic fatty acid wax admixed with one or more hydrophobic silicones. The preparation when topically applied to human skin exhibits surprising enhanced water repellency and skin conditioning effects while substantially eliminating the greasy appearance and tacky feel normally associated with water barrier products. The preparation is uniquely adapted for use as a diaper cream in that it combines moisturization with water resistance thereby substantially reducing incidents of diaper rash.

Accordingly, it is a prime object of the present invention to provide a new and improved water resistance cream conditioner.

Another object of the present invention is to provide a unique skin protective composition providing enhanced water repellancy and skin conditioning properties without a greasy appearance or a tacky feel.

A further object of the present invention is to provide a novel and unique cream conditioner especially useful in mitigating the effect of diaper rash on newborns and infants.

Still another object of the present invention is to provide a new and improved water resistant composition into which conventional sun blockers can be readily incorporated to provide a non-greasy, non-tacky sunscreen material.

These and still further objects as shall hereinafter appear are fulfilled by the present invention in a remarkably unexpected fashion as will be readily discerned from a careful consideration of the following detailed description of exemplary embodiments thereof.

DESCRIPTION OF PREFERRED EMBODIMENTS

The present invention relates to a pharmaceutical/cosmetic preparation and more particularly to a cream/lotion base containing a synthetic aliphatic wax, that is, a high molecular weight $C_{18}$–$C_{36}$ saturated synthetic fatty acid wax such a Syncrowax ® or an equivalent thereof developed for such use, admixed with one or more hydrophobic silicones, such as, cyclomethicone, dimethiconol, dimethicone, phenyltrimethicone, and the like.

The foregoing mixture forms a film when it is topically applied to a surface. The film thus formed is resistant to wetting by moisture. Further, as will appear, the base composition of the present invention far superior water barrier properties than can be obtained with the quaternaries; cationic polymer resins and gums heretofore employed as waterproofing agents. Further, no flaking or leaching of the product occurs even during extended use. An important factor of this new combination of ingredients is that it provides a silky and non-greasy lubricant which enables the active ingredient disposed therein to be spread evenly and smoothly upon the skin.

The amount of $C_{18}$–$C_{36}$ aliphatic saturated fatty acid wax and hydrophobic silicones used in this composition can, as will appear, vary greatly depending on the degree of waterproofing and skin feel desired for a particular product.

Preferably, the $C_{18}$–$C_{36}$ saturated synthetic fatty acid wax will range from about one to about ten percent by weight of the total composition and the hydrophobic silicones will vary from about two to about twenty percent by weight.

A number of film-forming agents, polymers, and cosmetic resins can be employed in combination with the present base formulation when product design considerations warrant their inclusion. Such agents, polymers and resins include: polyvinylpyrrolidone; PVP/eicosene copolymer; vinylpyrrolidone/vinyl acetate copolymers in which the monomer ratio ranges from 70/30 to 30/70; vinyl acetate/unsaturated carboxylic acid copolymers, for example 90% of vinyl acetate and 10% of crotonic acid; terpolymers of methyl methacrylate/stearyl methacrylate/stearyl methacrylate/dimethyl-aminoethyl methacrylate which have been completely quaternised with dimethyl sulphate, the monomers being used particularly in the ratio 20/23/57; a terpolymer of vinyl acetate/allyl stearate/allyloxyacetic acid, especially in the ratio of 80/15/5; maleic anhydride/methyl vinyl ether copolymers such as "Gantrez AN" and the ethyl, isopropyl and butyl esters thereof; and maleic anhydride/butyl vinyl ether copolymers. Another unexpected advantage of the present invention occurs when those polymers which are known to produce a sticky or tacky feel in conventional cream bases are used in the present invention, they create a smooth and silky composition which is neither tacky nor sticky.

For pharmaceutical preparations, a number of medications may be employed as an active ingredient when uniformly dispersed throughout the cream-conditioner of the present invention including steroids, such as, hydrocortisone, betamethasone and the like; antibiotics, such as bactimycin, erythromycin, and the like; antifungals such as, tolnaftate, clotrimazole, and the like; and other popular topical reagents such as benzoyl peroxide for the treatment of acne; diethyltoluamide for insect repellency and the like.

A prototype water barrier cream embodying the present invention to provide water repellency and conditioning can be formulated as follows:

| Ingredient | % (w/w) |
|---|---|
| Mineral Oil | 67-87 |
| Syncrowax ® HRS-C | 1-2 |
| Syncrowax ® HGL-C | 1-4 |
| Hydrophobic silicones (Q₂1401) | 5-20 |
| Silica | 6 |
| dl-alpha tocopherol | .1-1 |

To prepare the cream conditioner base of the present invention for sunscreen application, several ultraviolet absorbing sunscreen agents can be incorporated therein with good product stability. The agents include oxybenzone (2-hydroxy-4-methoxy-benzo-phenone); dioxybenzone (2,2'-dihydroxy-4-methoxy-benzophenone); amino benzoic acid; cinoxate (2-ethoxyethyl-p-methoxycinnamate); diethanol-amine-p-methoxycinnamate; digalloyl trioleate ethyl 4-bis (hydroxypropyl) aminobenzoate; 2-ethylhexyl-2-cyano-3,3-diphenylacrylate; ethylhexyl-p-methoxycinnamate; 2-ethylhexyl salicylate; glyceryl aminobenzoate; homosalate (3,3,5-trimethylcyclohexyl salicylate); triethanolamine salicylate; 2-phenylbenzimidazole-5-sulfonic acid; sulisobenzone (2-hydroxy-4-methoxybenzophenone-5-sulfonic acid); Padimate A (amyl-p-dimethylaminobenzoate); Padimate O (octyl dimethyl para aminobenzoate); 4-t-butyl-4'-methoxy-dibenzoylmethane; the combination of 2-hydroxy-1, 4-naphthoquinone with dihydroxyacetone; and menthyl anthranilate.

In one practice of the present invention, a suitably sized stainless steel tank is charged with mineral oil and the dual mixers (the sweep rotating at about 10 RPM clockwise while the turbine rotates at about 12 RPM counterclockwise) are activated.

Next, the batch is heated to 110° C. and, while heating, Syncrowax ® is added (sweep at 14 RPM and turbine at 24 RPM) until it is completely and homogeneously dispersed. When desired for formulation purposes, other waxes or fatty alcohols will be added at this time while turbine rotation is maintained.

Next, the silica or other thickener such as stearalkonium hectorite, propylene carbonate and the like is added to the batch while the mixers are maintained at the higher speed and the temperature is maintained above 78°-80° C. for one hour. Thereafter, with continued stirring, a suitable antioxidant, such as dl-alpha-tocopherol, is added to the batch and blended therethrough.

The batch is then cooled at a rate of about 0.5° C./minute. When a temperature of 40°-50° C. is reached, the hydrophobic silicone (Dow Q21401) is added with continuous mixing until the batch reaches room temperature, i.e., from about 10° to about 25° C. The batch, subject to Quality Control approval, is now ready for packaging.

To further aid in the understanding of the present invention and not by way of limitation, the following examples are presented.

EXAMPLE I

A suitably sized stainless steel tank is charged with mineral oil and the dual mixers (the sweep rotating at about 10 RPM clockwise while the turbine rotates at about 12 RPM counterclockwise) are activated.

Next, the batch is heated to 110° C. and, while heating, Syncrowax ® is added (sweep at 14 RPM and turbine at 24 RPM) until it is completely and homogeneously dispersed. When desired for formulation purposes, other waxes or fatty alcohols will be added at this time while turbine rotation is maintained.

Next, the silica or other thickener such as stearalkonium hectorite, propylene carbonate and the like is added to the batch while the mixers are maintained at the higher speed and the temperature is maintained above 78°-80° C. for one hour. Thereafter, with continued stirring, a suitable antioxidant, such as dl-alpha-tocopherol, is added to the batch and blended therethrough.

The batch is then cooled at a rate of about 0.5° C./minute. When a temperature of 40°-50° C. is reached, the hydrophobic silicone (Dow Q21401) is added with continuous mixing until the batch reaches room temperature, i.e., from about 10° to about 25° C. The batch, subject to Quality Control approval, is now ready for packaging.

EXAMPLE II

Using the foregoing procedure of Example I, a lip moisture stick embodying the present invention was prepared having the following composition (in weight percent). The ingredients, other than the synthetic aliphatic wax and hydrophobic silicones which are key, are shown as representative and know equivalents may be substituted for any of the listed non-key ingredients throughout these Examples.

| Lip Moisture Stick | % (w/w) |
|---|---|
| Syncrowax ® HGL-C | 12 |
| Hydrophobic silicones | 15 |
| Stearyl alcohol | 20 |
| Castor oil | 25 |

-continued

| Lip Moisture Stick | % (w/w) |
|---|---|
| Cetyl Alcohol | 3 |
| Mineral Oil | 25 |

EXAMPLE III

Using the procedure of Example I, a water proof sunscreen cream was prepared having the following composition (in weight percent):

| | |
|---|---|
| Mineral Oil | 39.5–78 |
| Octyl methoxycinnamate | 1–7.5 |
| Syncrowax ® HRS-C | 5–10 |
| Benzophenone-3 | 1–5 |
| Silica | 2–10 |
| Hydrophobic silicone | 5–15 |
| Stearalkonium hectorite and propylene carbonate | 1–6 |

EXAMPLE IV

Using the procedure of Example I, a medicated cream was prepared having the following composition (in weight percent):

| Medicated cream | % |
|---|---|
| Hydrocortisone | 0.5 |
| Mineral Oil | 62.5 |
| Syncrowax ® HRS-C | 2 |
| Syncrowax ® HGL-C | 4 |
| Silica | 6 |
| Hydrophobic silicone Q21401 | 15 |
| Hydrophobic starch | 10 |

EXAMPLE V

Using the procedure of Example I, a water barrier cream was prepared having the following composition (in weight percent):

| Water Barrier Emulsion | |
|---|---|
| Water | 80.50 |
| Syncrowax ® HGL-C | 3.5 |
| Glyceryl stearate and PEG 100 stearate | 2 |
| Sorbitan stearate | 2 |
| Polysorbate 60 | 2 |
| Hydrophobic silicone Q21401 | 10 |

EXAMPLE VI

Using the procedure of Example I, a prototype diaper cream formula was prepared and thereafter clinically tested at the Pediatric Clinic of Paris Hospital in France. The test formula (in weight percent) consisted of:

| | |
|---|---|
| Mineral oil | 59.66 |
| Aliphatic waxes | 5.34 |
| Hydrophobic silicone | 14.00 |
| PVP/eicosene copolymer | 2.00 |
| Dry-flo starch | 13.00 |

All cases tested showed surprising improvement or suppression of symptoms related to dryness, itching and redness of the buttocks of the babies. This was only after five days of application.

| Formula # | Number of patients tested | Improvement |
|---|---|---|
| 276-2 | 6 | >75% |
| | 2 | >95% |
| | 2 | >50% |
| 75-5 | 6 | >75% |
| | 1 | >95% |
| | 2 | >50% |
| 77-1 | 5 | >75% |
| | 2 | >95% |
| | 1 | >50% |
| 79-1 | 6 | >75% |
| | 2 | >95% |
| | 1 | >50% |

EXAMPLE VII

A sun screen cream was prepared according to Example III and tested according to the procedures and the criteria outlined in the "Proposed Monograph for OTC Sunscreen Drug Products" issued by the F.D.A. on Aug. 25, 1978 (43 Fed. Reg. 166 at 38206–38269).

The purpose of the tests was to determined the Sun Protection Factor (SPF) efficacy on the skin of human subjects, before and after a total of 80 minutes of water immersion.

The wet control test material, Johnson & Johnson SUNDOWN ™ moderate (SPF=4), and the static control, 8% Homosalate, were prepared according to FDA specifications (Fed. Reg., Ibid at 38259). The test product was prepared according to Example III.

The light source was a Solar Ultraviolet Simulator, Model 10S (Fed. Reg., Ibid at 38260) consisting of a 150 watt Xenon arc lamp with all required optical elements and a regulated power supply.

A total of five fair skinned subjects (all female, age range 28 to 60) with skin types I, II, and III were placed on test.

Testing was preformed using the following procedures.

Test Site Inspection

The physical examination determined the presence of sunburn, suntan, scars, active dermal lesions, and uneven skin tones on the areas of the back to be tested. The presence of nevi, blemishes or moles was acceptable if they would not interfere with the study results. Excess hair on the back, if present, was shaved.

Test Site Area

A test site area served as an area for determining the subject's Minimal Erythema Dose (MED) after application of either the sunscreen product or for determining the subject's MED of unprotected skin (control site). The subject's MED is the time of exposure that produces the minimally perceptible erythema at 16 to 24 hr post-exposure. The area to be tested was the back between the beltline and the scapulae (shoulder blade) and lateral to midline. The test site areas were horizontal or vertical, and rectangular or square. Each test site area for applying a product or standard control was 50 cm sq. These test sites were outlined with gentian violet while the person to be tested was in an upright position.

Test Subsite Area

Each test site area of the test was divided into seven subsite test areas that were at least 1 cm sq. For both the test product and the control product, two test site areas were used—one for before water immersion and one for after 80 minute water immersion. Placement of test site areas were randomized among the subjects. One additional test site area was used for 8% HMS SPF determination on each subject as per FDA Proposed Monograph.

Application of the Test Material

To insure standardized reporting and to define a product's Sun Protection Factor (SPF) value, the application of the product is expressed on a weight basis per unit area which establishes a standard film. The test sunscreen product and the sunscreen standard application is 2 mg/cm sq or 2 ul/cm sq. The 50 cm sq test site area requires 100 mg of a product or 100 ul (assuming a specific gravity of 1) to obtain a standard 2 mg/cm sq test application. For the test product, a cream, the viscosity is such that the material was weighed and applied to the appropriate areas by spreading with a finger cot.

Waiting Period

Before exposing the test site areas after applying a product, a waiting period of at least 15 minutes was employed.

Test Site Irradiation

A series of UV light exposure (units of time) were administered to the subsites on each subject with the solar simulator. One series of exposures was administered to the untreated, unprotected skin to determine the MED. The MED is the time of exposure that produces the minimally perceptible erythema at 16 to 24 hour post-exposure. The MED of the subject's unprotected skin was determined prior to the test day, then again on test day.

Each of the protected test sites (controls and/or test sunscreen product) were also exposed to UV light. The standard time intervals selected are a geometric series represented by (1.25)n, wherein each exposure time interval is 25 percent greater than the previous time. (The reason for using the geometric sequence of UV exposure is to maintain the same relative uncertainty, expressed as a constant percentage), independent of the subject's sensitivity to UV light, regardless of whether the subject has a high or low MED). The exact series of exposures to be given was determined by the MED of the unprotected skin.

After UV irradiation of one test site each for both the test sunscreen and the above-cited control sunscreens, each subject entered the whirlpool for 20 minute; whirlpool agitation was at a moderate level. This was followed by a 20 minute rest period, followed by a second 20 minute period of activity in the whirlpool, followed by a second 20 minute rest period, followed by a third 20 minute period of activity in the whirlpool, followed by a third 20 minute rest period, followed by a fourth 20 minute period of activity in the whirlpool. Care was taken and each subject was continuously monitored to insure that the "after" test site areas were untouched. At the conclusion of the 80 minute water tests, the test sites were air dried without toweling. The second protected test site of both the test sunscreen and the above cited control was then exposed to UV light, using the identical method and series of exposures as were used for the "before" UV light irradiation.

Each subject reported back at 16 to 24 hours postexposure, at which time each test site area was read to determine the Minimal Erythema Dose (MED) of both the unprotected and the protected skin.

For both the test sites irradiated prior to water immersion and the test sites irradiated after 80 minutes water immersion, the SPF of the test sunscreen is then calculated from the exposure time interval required to produce the MED of the protected skin, and from the exposure time interval required to produce the MED of the unprotected skin (control site), i.e., $$SPF = \frac{MED \text{ Protected Skin}}{MED \text{ Unprotected Skin}}$$

Results and Conclusions

No adverse reactions were observed in any of the subjects who were tested as per the testing procedures described above. The Sun Protection Factor (SPF) value for the sunscreen, as well as for the controls, are as follows:

| Product | SPF | SPF Labeling Category |
|---|---|---|
| 95-90-03 | | |
| Before Immersion | 16.70 | 15.00 or greater (Ultra) |
| After Immersion | 16.70 | 15.00 or greater (Ultra) |
| Controls | | |
| J&J SUNDOWN Moderate | | |
| Before Immersion | 5.00 | 4.00 to 5.99 (Moderate) |
| After Immersion | 4.60 | 4.00 to 5.99 (Moderate) |
| 8% Homosalate | 4.40 | 4.00 to 5.99 (Moderate) |

From the foregoing, it is apparent that new and useful water resistant composition has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended here.

Accordingly, what is claimed is:

1. An anhydrous topical composition of matter for water proofing mammalian skin containing a pharmacologically acceptable carrier selected from the group consisting of mineral oil, vegetable oil, and an aliphatic/branched chain ester and, in weight percent, from about 1 to about 10 percent $C_{18}$-$C_{36}$ saturated synthetic fatty acid wax and from about 2 to about 20 percent anhydrous hydrophobic silicone, said wax and said silicone being dispersed in said carrier.

2. A composition according to claim 1 in which said hydrophobic silicone is selected from the group consisting of: cyclomethicone; dimethicone; phenyltrimethicone; dimethiconol; and mixtures thereof.

3. An anhydrous topical composition containing in weight percent from about 67 up to about 87 percent mineral oil, from about 2 up to about 6 percent ($C_{18}$-$C_{36}$) saturated synthetic fatty acid wax, from about 5 percent up to about 20 percent hydrophobic silicone; about 6 percent silica; and from about 0.1 up to about 1 percent dl-alpha tocopherol.

4. A composition of matter according to claim 3 in which said hydrophobic silicone is selected from the group consisting of: cyclomethicone; dimethicone; phenyltrimethicone; dimethiconol; and mixtures thereof.

* * * * *